United States Patent [19]

Howarth et al.

[11] Patent Number: 4,845,421

[45] Date of Patent: Jul. 4, 1989

[54] METHOD AND APPARATUS FOR MEASURING THE MOISTURE CONTENT OF A SUBSTANCE

[75] Inventors: Walter J. Howarth; Laurance Jarvis, both of Forestville, Australia

[73] Assignee: Mineral Control Instrumentation Ltd., Forestville, Australia

[21] Appl. No.: 107,367

[22] Filed: Oct. 9, 1987

[30] Foreign Application Priority Data

Oct. 10, 1986 [AU] Australia ............... PH8466

[51] Int. Cl.⁴ .................................... G01R 27/26
[52] U.S. Cl. .................. 324/61 R; 73/335; 73/336.5
[58] Field of Search ............ 324/61 R; 73/335, 336, 73/336.5

[56] References Cited

U.S. PATENT DOCUMENTS

| | | | |
|---|---|---|---|
| 3,211,171 | 11/1965 | Locher | 324/61 R |
| 3,528,287 | 9/1970 | Melcher | 324/61 R |

FOREIGN PATENT DOCUMENTS

| | | | |
|---|---|---|---|
| 969617 | 6/1975 | Canada | 324/61 R |
| 2021811 | 3/1971 | Fed. Rep. of Germany | 324/61 R |
| 2037157 | 9/1971 | Fed. Rep. of Germany | 324/61 R |

Primary Examiner—Reinhard J. Eisenzopf
Assistant Examiner—Maura K. Regan
Attorney, Agent, or Firm—McAulay Fisher Nissen & Goldberg

[57] ABSTRACT

The moisture content of a substance (1) on a moving belt (2) is measured as a function of dielectric constant. Two pairs of electrodes (4), (5) are positioned adjacent the belt, an inner pair of electrodes (4) and an outer pair (5), an A.C. potential is applied to the electrodes, the flux from the outer pair (5) passing through the substance (1) at a greater distance than the flux from the inner pair (4).

3 Claims, 5 Drawing Sheets

METHOD AND APPARATUS FOR MEASURING THE MOISTURE CONTENT OF A SUBSTANCE

This invention relates to a method and apparatus for measuring the moisture content of a substance.

BACKGROUND OF THE INVENTION

Where a substance of volume of material is of relatively uniform moisture content, it is relatively easy to obtain a representative sample thereof and to measure the moisture content of that sample in order to obtain knowledge of the moisture content of the volume of the substance.

However, where it is required to determine the moisture content of a continuous flow of substance during production or a processing operation of that substance, further difficulties arise due to the variation of the moisture content of the substance along its travel, and more particularly to the variation of the moisture content in the depth of the substance together with variations of the depth of the substance itself.

In U.S. Pat. No. 4,468,610 there is described an apparatus for measuring the moisture content of gypsum board and like products, and in this instance the gypsum board is of regular thickness and density, and the moisture content does not readily vary through the thickness of the board itself.

In Australian Patent Specification No. 52496/86 there is described a method and apparatus for producing a signal or signals related to the moisture content of a substance as it travels along a conveyor belt, this apparatus utilizing a single pair of spaced electrodes located remote from the substance whereby an A.C. field generated therebetween passes through the substance and means measuring an A.C. signal related to a field passing through the substance to derive a moisture output signal therefrom related to the moisture content of the substance. Also that Patent specification describes an apparatus for producing signals related to the density or thickness of the substance and these two apparatuses are combined within the one unit in order to provide a signal representative of the moisture content of the substance.

BRIEF STATEMENT OF THE INVENTION

It is an object of this invention to provide a method and apparatus for determining the moisture content of a substance or material travelling on a belt which gives an indication of the moisture content thereof without having to provide an apparatus for measuring the thickness or density of that material, or which gives improved results when used in conjunction with an apparatus for measuring the thickness or density of the material.

Thus there is provided according to the invention a method and apparatus for the measurement of the moisture content of a substance as a function of dielectric constant by the use of a plurality of pairs of electrodes spaced from said substance, a first of said pairs of electrodes being positioned centrally of said plurality of pairs, and with said next pair or electrodes being positioned one on each side of said central pair, whereby the application of an electrical potential to said pairs of electrodes, the flux from said next pair of electrodes measures the moisture content at a greater distance than the flux from the central pair.

BRIEF DESCRIPTION OF THE DRAWINGS

In order to more fully describe the invention reference will now be made to the accompanying drawings in which.

DESCRIPTION OF THE PREFERRED EMBODIMENT

Figure 1:
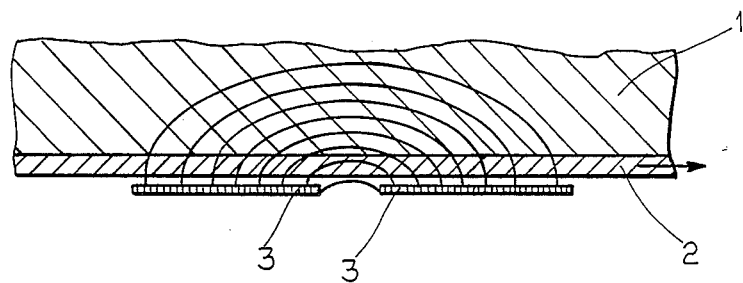
FIG. 1 is an example of the known electrode configuration of the prior art.

Referring to FIG. 1 there is shown a known method for measuring the moisture content of a material 1 travelling on a belt 2, with a pair of capacitor plates 3 being disposed under the belt, the capacitance between the plates varying in accordance with the changes in the dielectric constant of the material on the belt. Since water has a dielectric constant of about 80 and most materials which are to be measured have a dielectric constant of less than 6, it is clear that variations in the moisture content will have a strong influence on the measured capacitance.

Due to the fact that the height and packing density of the material and the belt are variable, there are problems in obtaining accurate results. This situation can be improved by combining the moisture content measurements with the measurements of mass per unit area and bulk density using nucleonic techniques as disclosed in the Australian specification No. 52496/86 referred to above.

An increase in accuracy can be obtained by increasing the sophistication of the capacitance measurement in order to obtain additional information.

Figure 2:
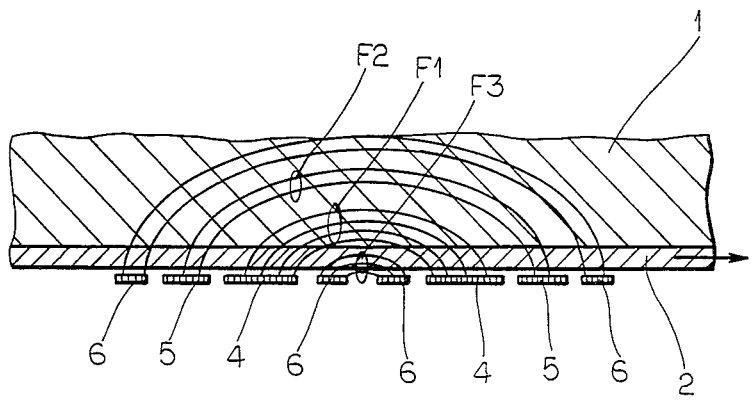
FIG. 2 is an illustration of a pair of electrodes in a split plate configuration.
Figure 3:
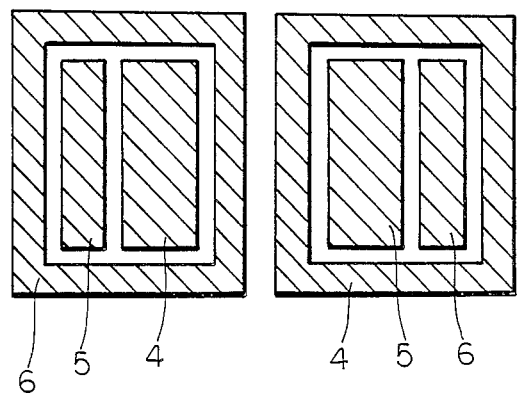
FIG. 3 is a plan view of the electrodes of FIG. 2.

As shown in FIGS. 2 and 3, the capacitor plates can be split into two separate plates, or into two pairs of plates 4, 5 and surrounded by a guard electrode 6 as illustrated in FIGS. 2 and 3.

Referring to FIG. 2, it will be seen that the flux F1 between the inner pair of plates 4 passes through the lower portion of the material 1 on the belt 2, while the flux from the outer pair of electrodes 5 passes at a higher level through the material 1 on the belt 2, thus in effect passing through all material on the belt. The flux between the guard electrodes is shown as F3.

As shown in FIG. 3 the inner pair of plates 4 are separated by guard electrodes 6 and guard electrodes 6 are positioned outside the outer pair of plates 5 with the inner and outer guard electrodes on each side being joined 7 to form a generally rectangular guard electrode.

Figure 4:
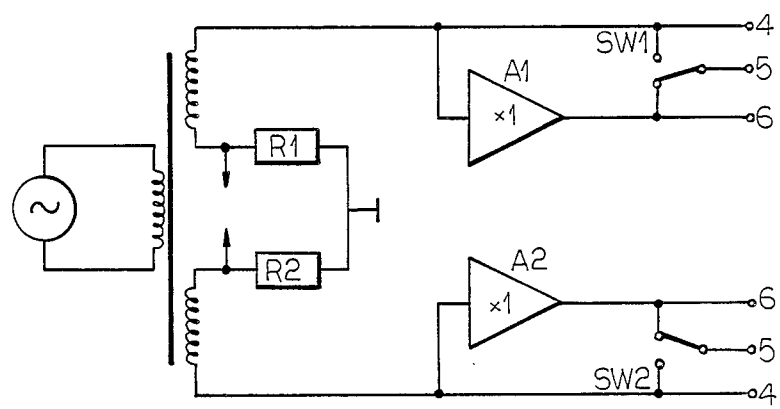
FIG. 4 is a schematic electrical diagram of the electrode connections.

Referring now to FIG. 4, the way in which the various electrodes are connected is illustrated in the simplified schematic shown.

The inner electrodes are driven with high frequency sinewaves (6.144 MHz) of equal amplitude and opposite phase via a transformer TF1 whose secondaries are balanced with respect to earth. The guard electrodes are driven with signals from the same source but after buffering by the unity gain amplifiers A1 and A2. The outer electrodes are switched electronically by SW1 and SW2 at a 1 KHz rate so that for half of each cycle, they are connected to the inner electrodes and for the other half they are connected to the guard electrodes.

The capacitance measurement is carried out as follows. The amplitude of the high frequency input to the transformer is controlled so that the voltages applied to the electrodes are constant at all times. Hence, the current flowing between the inner electrodes is proportional to the admittance seen by the electrodes. This current flows also through two resistors R1 and R2 which are connected in series within the transformer secondary windings. Hence the voltages V1 and V2 which are developed across these resistors are also proportional to the admittance seen. The component of these voltages which has a phase of 90 degrees with respect to the drive signal is measured by a synchronous detector to determine the susceptance and hence the capacitance seen by the electrodes.

Due to the buffering provided by A1 and A2, current flowing in the guard electrodes does not flow in R1 and R2 and does not contribute to the measured result. Current flowing in the outer electrodes will also provide no contribution to the measured capacitance while SW1 and SW2 connect them to the guard electrodes. However, during the alternate half cycles, when they are connected to the inner electrodes, they will make a contribution to the measured capacitance.

Referring to FIG. 2, it can be seen that the electric flux flowing between the guard electrodes is to a large extent outside of the material being measured. The flux between the inner electrodes penetrates the lower part of the material on the belt while the flux between the outer electrodes extends further into its upper region.

Figure 5:
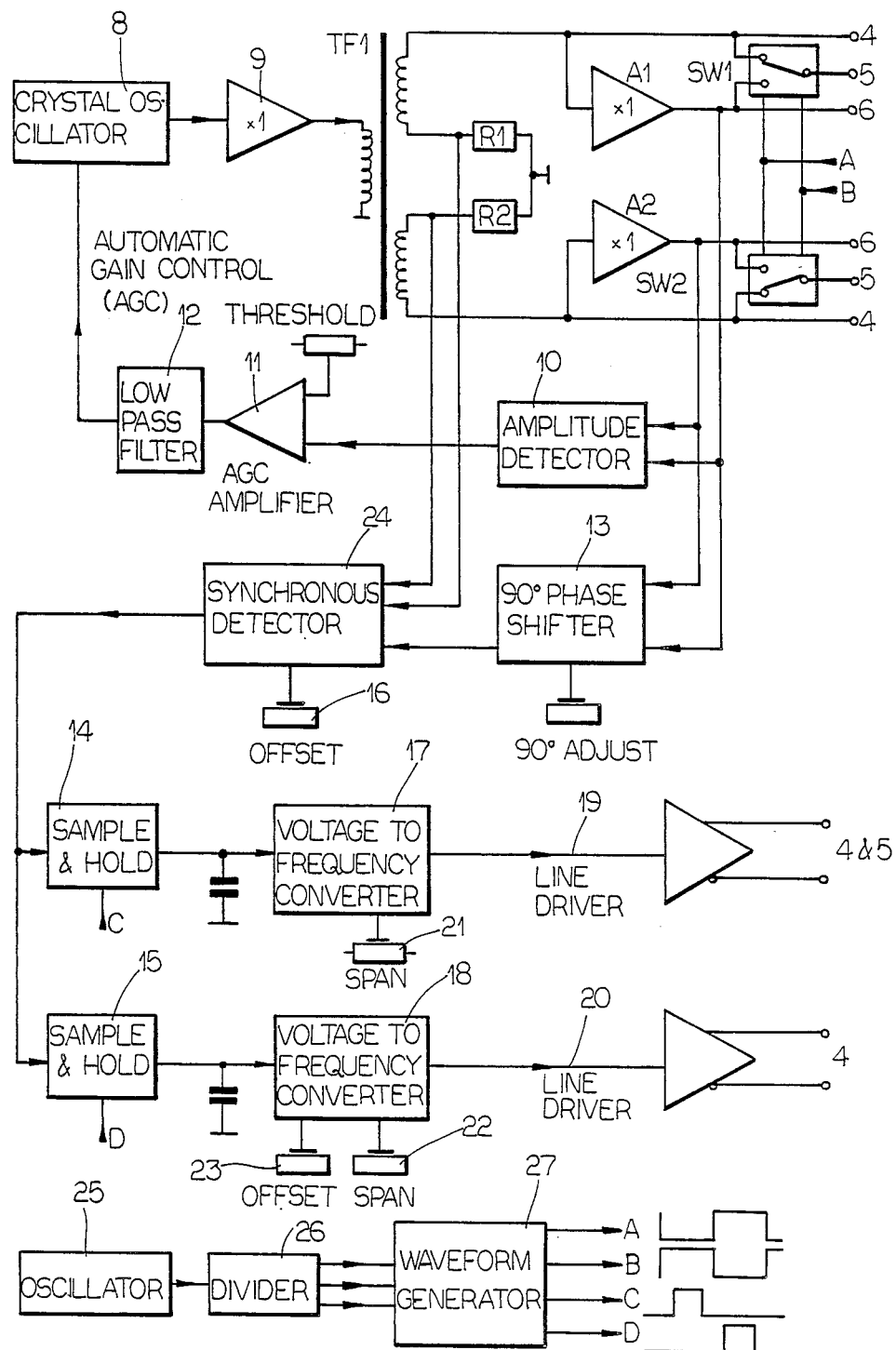
FIG. 5 is a circuit block diagram.

The total circuit configuration is illustrated in the block diagram of FIG. 5.

The 6.144 MHz crystal oscillator 8 drives the transformer FT1 via a unity gain buffer amplifier 9. The electrode drive configuration has already been described in the previous section. The sum of the amplitudes of the signals fed to the guard electrodes is measured in a synchronous detector 10. The resulting direct voltage is compared with a preset threshold voltage and the difference is amplified by the automatic gain control AGC amplifier 11. After filtering 12, the output of the AGC amplifier is used to control the amplitude of the crystal oscillator 8 so that a constant level appears on the electrodes.

The outputs of the guard buffer amplifiers A1, A2 are also used as inputs to a network which provides the 90 degree phase shift 13 (potentiometer adjustable) for the capacitance synchronous detector 24. Signal inputs for the detector are taken from the measuring resistors R1 and R2 connected in series with the transformer secondaries.

The synchronous detector output is separated into two DC levels by two sample and hold circuits 14, 15 controlled by the gating waveforms C and D. One output represents the sum of the capacitance seen by the inner and outer electrodes while the other corresponds to the inner electrodes alone.

An offset potentiometer 16 at the synchronous detector is used to set the output voltage range to −1 to −5 volts corresponding to a measured capacitance of 0 to 7.5 pF. For transmission to the measuring system's computer, the voltage levels are converted 17, 18 to pulses having frequencies in the range of 1 to 5 KHz. The resulting pulse trains are transmitted on balanced lines 19, 20 according to the RS422A standard. Potentiometer adjustments are provided for the span 21, 22 of each voltage-to-frequency converter to set its sensitivity to 1 KHz per volt. In addition, an offset adjustment 23 is provided for the inner electrode only channel so that both channels can give an output of 1 KHz when nothing is connected to the measuring circuit.

The various control waveforms required are all derived from a common 16 KHz oscillator 25 and a divider chain 26 providing 4, 2 and 1 KHz signals. Further waveform generating circuitry 27 produces the four required waveforms A, B, C and D (see FIG. 5) via buffer amplifiers. A and B are 1 KHz square waves with opposite phases used to switch the outer electrodes between the guards and the inner electrodes. Waveforms C and D are narrower pulses used to gate the two sample and hold circuits.

Thus it will be seen that the essential concept of the invention is that of using two pairs of capacitor plates so that one pair can look further into the material being measured than the other. However, it is to be realized also that the number of electrode pairs could be increased to give more channels of information, each of which probes to a different height into the materials being measured. Moreover, the switching of the pairs of electrodes could be arranged in different ways. For example, the outer electrodes could be connected continuously while the inner electrodes are switched or both pairs of electrodes could be switched during alternate half cycles.

Also while guard electrodes have been described, and are desirable, the guard electrodes are not absolutely essential. The main function of the guard electrodes is to reduce the amount of electric flux which flows other than in the material being measured, and which therefore swamps to some extent the wanted flux.

Although electrode shapes have been shown as being generally rectangular shapes, proportions and sizes could be varied to suit other applications. The electrode axis of symmetry could be at right angles to, parallel to or even at some other angle to the direction of flow of the material being measured, it being realized also that the method could be applied to static measuring systems as well as materials moving on a belt. Thus for example the capacitor plates could be orientated vertically instead of horizontally, for example to measure the dampness in a wall.

Figure 6A:
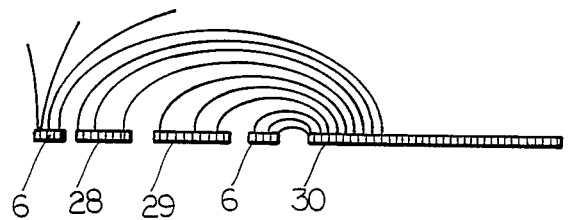
FIG. 6a is an elevation and FIG. 6B is a plan view of a further form of the invention.
Figure 6B:
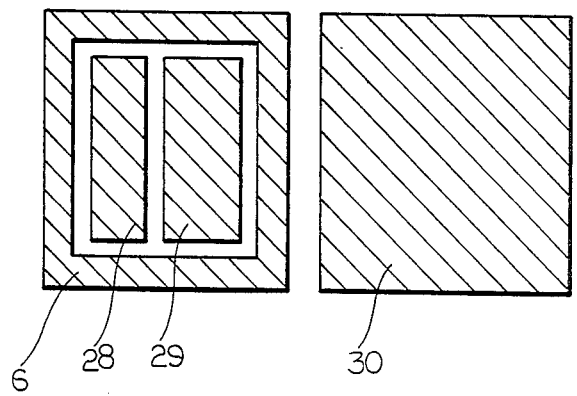
Figure 7A:
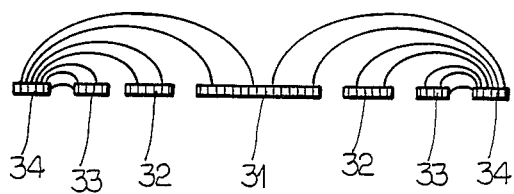
FIG. 7a is a still further form of the invention.
Figure 7B:
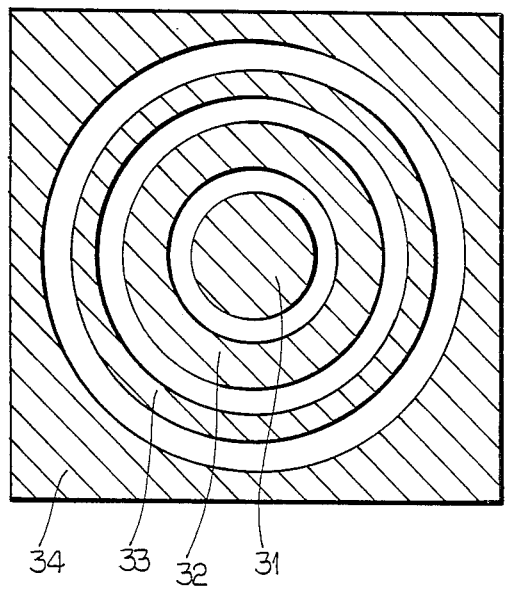
FIG. 7b is a plan view of a still further form of the invention.

Referring to FIG. 6 there is shown a single ended electrode configuration in rectangular shape with the capacitor plates 28, 29 being fed signals which are balanced with respect to ground 30 and FIG. 7 shows a further alternative in which a single ended circular electrode configuration is utilized having outer plate 31, inner plate 32, guard plate 33 and ground plate 34.

Circuit configurations other than that described could be used for the capacitance measurement, including unbalanced configurations when using unbalanced electrode configurations.

Also it is to be realized that the measurements could be performed at a variety of frequencies either sequentially with one set of electrodes, or simultaneously with more than one set of electrodes.

Although various forms of the invention have been described in some detail it is to be realized that the invention is not to be limited thereto but can include various modifications falling within the spirit and scope of the invention.

The claims defining the invention are as follows:

1. A method of measuring the moisture content of a substance as a function of dielectric constant, comprising the steps of:

providing a partiality of pairs of electrodes spaced from said substance, a first of said pairs of electrodes being positioned centrally of said plurality of pairs, with a next pair being positioned one on each side of said first pair, and guard electrodes surrounding said pairs of electrodes;

applying A.C. electric potential to said pairs of electrodes, sequentially switching said pairs of electrodes to said guard electrodes; and sequentially measuring the current flowing between the electrodes of each pair, the flux from said next pair of electrodes passing through said substance at a greater distance than the flux from the central pair of electrodes.

2. Apparatus for measuring the moisture content of a substance as a function of dielectric constant, said apparatus comprising:

a plurality of pairs of electrodes spaced from said substance, a first of said pairs being positioned centrally of said plurality of pairs of electrodes with a next pair of electrodes having an electrode on either side of said pair of electrodes;

guard electrodes positioned between the first pair of electrodes and outside said next pair of electrodes;

an A.C. signal generator connected to apply high frequency sine waves to said pairs of electrodes, switching means alternatively connecting said pairs of electrodes to said guard electrodes and to measure the current flowing between the electrodes of each pair.

3. Apparatus as defined in claim 2, wherein the outputs from the said pairs of electrodes are passed through a synchronous detector, whose output is divided into two D.C. levels by two sample and hold circuits, one representing the sum of the capacitance seen by the inner and outer pairs of electrodes, and the other by the inner pair of electrodes alone.

* * * * *

UNITED STATES PATENT AND TRADEMARK OFFICE
CERTIFICATE OF CORRECTION

PATENT NO. : 4,845,421

DATED : July 4, 1989

INVENTOR(S) : Walter James HOWARTH et al.

It is certified that error appears in the above—identified patent and that said Letters Patent is hereby corrected as shown below:

Please add the name of the third inventor to this Letters Patent, as follows:

John Pope,
of Forestville, Australia

Signed and Sealed this

Sixteenth Day of October, 1990

*Attest:*

HARRY F. MANBECK, JR.

*Attesting Officer*     *Commissioner of Patents and Trademarks*